United States Patent
Kitamura et al.

(10) Patent No.: US 11,622,840 B2
(45) Date of Patent: Apr. 11, 2023

(54) OPAQUE IMPARTING LIQUID FOR ZIRCONIA

(71) Applicant: SHOFU INC., Kyoto (JP)

(72) Inventors: Toshio Kitamura, Kyoto (JP); Shuhei Takahashi, Kyoto (JP)

(73) Assignee: SHOFU INC., Kyoto (JP)

( * ) Notice: Subject to any disclaimer, the term of this patent is extended or adjusted under 35 U.S.C. 154(b) by 787 days.

(21) Appl. No.: 16/367,459

(22) Filed: Mar. 28, 2019

(65) Prior Publication Data

US 2019/0388196 A1  Dec. 26, 2019

(30) Foreign Application Priority Data

Mar. 30, 2018 (JP) .............................. JP2018-066937
Mar. 18, 2019 (JP) .............................. JP2019-049270

(51) Int. Cl.
| | | |
|---|---|---|
| *A61C 13/00* | (2006.01) | |
| *A61C 13/08* | (2006.01) | |
| *C04B 35/48* | (2006.01) | |
| *C04B 41/00* | (2006.01) | |
| *C04B 41/46* | (2006.01) | |
| *C04B 41/49* | (2006.01) | |
| *C09D 7/61* | (2018.01) | |
| *C09D 7/63* | (2018.01) | |
| *A61K 6/60* | (2020.01) | |
| *A61K 6/70* | (2020.01) | |

(52) U.S. Cl.
CPC ........ *A61C 13/0022* (2013.01); *A61C 13/082* (2013.01); *C04B 35/48* (2013.01); *C04B 41/009* (2013.01); *C04B 41/463* (2013.01); *C04B 41/49* (2013.01); *C09D 7/61* (2018.01); *C09D 7/63* (2018.01); *A61K 6/60* (2020.01); *A61K 6/70* (2020.01); *C04B 2235/3244* (2013.01); *C04B 2235/449* (2013.01)

(58) Field of Classification Search
None
See application file for complete search history.

(56) References Cited

U.S. PATENT DOCUMENTS

| | | | | |
|---|---|---|---|---|
| 1,891,440 A | * | 12/1932 | Harold ...................... | C14C 3/04 8/94.29 |
| 5,837,023 A | * | 11/1998 | Koike ................ | C03C 23/0095 65/17.2 |
| 2002/0156154 A1 | * | 10/2002 | Ando ..................... | C09D 11/18 523/160 |
| 2004/0106782 A1 | * | 6/2004 | Iwamoto .............. | C07D 221/18 546/61 |
| 2008/0103245 A1 | * | 5/2008 | Endo ................... | B41M 5/5218 524/543 |
| 2013/0115365 A1 | | 5/2013 | Wang et al. | |
| 2014/0253695 A1 | | 9/2014 | Kassouf | |

FOREIGN PATENT DOCUMENTS

| | | |
|---|---|---|
| CN | 105132897 | 12/2015 |
| CN | 107572568 | 1/2018 |
| JP | 2016-500955 | 1/2016 |

OTHER PUBLICATIONS

Extended European Search Report dated Nov. 4, 2019 in European Patent Application No. 19165193.4.

* cited by examiner

*Primary Examiner* — Stefanie J Cohen

(74) *Attorney, Agent, or Firm* — Wenderoth, Lind & Ponack, L.L.P.

(57) ABSTRACT

To provide a liquid material which can only adjust transparency by applying on a part of a zirconia crown having high transparency, without coloring.

The present disclosure provides an opaque imparting liquid used for a prosthesis device cut and machined from a dental zirconia for cutting and machining, comprising;
(a) 10 to 39 wt. % of a water-soluble aluminum compound and/or a water-soluble lanthanum compound,
(b) 60 to 89 wt. % of water, and
(c) 1 to 20 wt. % of an organic solvent.

17 Claims, No Drawings

OPAQUE IMPARTING LIQUID FOR ZIRCONIA

CROSS-REFERENCE TO RELATED APPLICATIONS

This application is based on and claims the benefit of priorities from Japanese Patent Application Serial No. 2018-066937 (filed on Mar. 30, 2018) and Japanese Patent Application Serial No. 2019-049270 (filed on Mar. 22, 2019), the contents of which are hereby incorporated by reference in their entirety.

BACKGROUND OF THE INVENTION

Field of the Invention

The present disclosure relates to an opaque imparting liquid to exhibit opaque property on a zirconia ceramic prosthesis device after sintering by applying to the prosthesis device cut and machined from a dental zirconia for cutting and machining by using a CAD/CAM system in a dental field.

Description of the Related Art

In the conventional dental treatment of a defect part of a dental crown, a prosthetic restoration using a casting crown bridge and an artificial tooth has been performed generally. Specific examples include a clinical application of a porcelain baked crown bridge which reproduces a tooth crown shape by baking porcelain material on a surface of a metal frame made from a casting alloy for porcelain baking and has both a functionality and aesthetic property.

In addition, from the point of view of the metal allergy and the price remarkable rise to depend on the noble metal market price and from the point of view of aesthetic property which can imitate a color tone of a natural tooth, a prosthesis device, which is so-called all ceramics, prepared by the dipping method using alumina, aluminosilicate glass, lithium disilicate glass and the like or by the press method using ceramic ingot, has attracted attention, and, the prosthesis restoration using it has been increased.

In recent years, techniques to prepare a prosthesis device by the cutting and machining which uses a dental CAD/CAM system spread rapidly and it has been becoming possible to easily prepare prosthetic devices by milling blanks such as a block and a disk which are made of zirconia, alumina, aluminosilicate glass, and lithium disilicate glass. In addition, although the zirconia has been frequently used in the clinical as high-strength ceramic, a zirconia blank (pre-sintered body) which has adjusted strength and hardness which are advantageous for cutting and machining and is prepared by pre-sintering (temporary calcined) at low sintering temperature is generally used. The zirconia blank which is the pre-sintered body is not subjected to the perfect sintering in order to improve cutting property in the zirconia blank.

Since this zirconia blank has the bending strength which is used in the frame of 4 or more units bridge, a tetragonal partially stabilized zirconia blank containing 3 mol % of yttrium oxide has been put to practical use. This zirconia blank containing 3 mol % of yttrium is added with a very small amount of alumina for improving sinterability and restraining the low temperature deterioration. In addition, in order to increase optical transparency and to use as a molar tooth full crown, a zirconia blank containing an infinitesimal alumina has been clinically used. In addition, in order to use as a front tooth full crown, a zirconia blank in which optical transparency is highly designed by increasing a content of yttrium oxide to 5-6 mol %, which is added as a stabilizer, also has been used.

Zirconia is broadly divided into two kinds including a white color tone zirconia and a colored zirconia where the color tone is toned to a color tone close to that of a natural tooth. In the color tone of the natural tooth, the color becomes darker from an incisal part corresponding to an enamel of the tooth toward a cervical portion, which is called a condition where the chroma increases.

Therefore, a technique to mold a dental zirconia blank for cutting and machining which has multilayered structure and is imparted with the gradation of the color prepared by superposing progressively a plurality of zirconia powders which have different color tones including a color tone corresponding to an enamel color of an incisal part and a color tone corresponding to a cervical portion color in a layer form in order to reproduce the color tones of the incisal part and the cervical portion of the natural tooth in a prosthesis device which is cut and machined from the dental zirconia blank has been used.

This dental zirconia blank for cutting and machining which has the multilayered structure has a feature that a plurality of layers having different color tones, optical transparency or the like are superposed at various thickness.

However, when a yttrium content of the zirconia blank is 5 mol % or more, although the transparency is improved, the strength decreases, and therefore there is a problem that breakage is caused when it is used for the case of 4 or more bridges.

On the other hand, when a yttrium content of the zirconia blank is within a range of 3 to 4 mol %, since sufficient transparency is not obtained, it is difficult to reproduce transparency corresponding to an enamel portion of a tooth. Therefore it is necessary to build a glass which is called as the porcelain to the enamel. However, this process is a very complicated process and requires the technique of the technician.

On the other hand, a trial to improve sintering property by incorporating 0.2 to 2 wt. % of alumina into a zirconia containing 3 mol % of yttrium for the purpose of improving strength has been performed. However, there is a problem that sufficient transparency is not obtained in the zirconia containing alumina.

As described above, the improvement of the translucency of a dental zirconia material to be close to the translucency of the natural tooth has been tried so far. However, the part called an abutment tooth used in a dentistry include a metal abutment, a discolored tooth or the like. In the case of a transparent zirconia, there is a problem that it is easily affected by the color tone of the abutment tooth. In the case of using an opaque zirconia, although the influence of an abutment tooth decreased, there is a problem that transparency of an enamel layer is not enough. Therefore, it has been necessary to having an opaque function which can impart slightly opacity only to the part of the abutment tooth.

On the other hand, there is a method for adding a color to a semi-sintered zirconia in imitation of an abutment tooth by a coloring material. Some of this method exhibit an opaque effect by applying water-soluble solution of titanium, however there is a problem that titanium causes cloudiness in sintering and properties are decreased.

Japanese Unexamined Patent Application Publication (Translation of PCT Application) No. 2016-500955 discloses a preparing method of a zirconia having a color tone which is closes to the color tone of the tooth by applying a coloring material to a pre-sintered body of the zirconia. In this method, the transparency is improved by coloring a surface of the zirconia, however, the coloring material is used, it is impossible to adjust darkness for adjusting opacity.

SUMMARY OF THE INVENTION

Technical Problem

In the above described prior arts, although a coloring effect is exhibited, it is impossible to impart opacity only to a portion where an adjustment of transparency is desired. A problem to be solved by the present disclosure is to provide a liquid material which can only adjust transparency by applying on a part of a zirconia crown having high transparency, without coloring. In addition, a zirconia crown without decreasing strength after sintering is provided by applying this liquid material.

Solution to Problem

The present disclosure provides an opaque imparting liquid used for a prosthesis device cut and machined from a dental zirconia for cutting and machining, comprising;
(a) 10 to 39 wt. % of a water-soluble aluminum compound and/or a water-soluble lanthanum compound,
(b) 60 to 89 wt. % of water, and
(c) 1 to 20 wt. % of an organic solvent.

In the opaque imparting liquid of the present disclosure, it is preferable that the organic solvent (c) contains any of alcohols, polyol and glycol ethers. In the opaque imparting liquid of the present disclosure, it is preferable that the organic solvent (c) is any of alcohols, polyol and glycol ethers.

In the opaque imparting liquid of the present disclosure, it is preferable that the water-soluble aluminum compound and/or the water-soluble lanthanum compound (a) contains aluminum acetate and/or lanthanum acetate. In the opaque imparting liquid of the present disclosure, it is preferable that the water-soluble aluminum compound and/or the water-soluble lanthanum compound (a) is aluminum acetate or lanthanum acetate.

In the opaque imparting liquid of the present disclosure, it is preferable that the dental zirconia for cutting and machining is colored by a zirconia powder where iron, erbium, cobalt or the like is solid-solved.

The present disclosure provides an opaque imparting method comprising; applying the opaque imparting liquid of the present disclosure only to an inner surface of a prosthesis device cut and machined from a dental zirconia for cutting and machining.

In the opaque imparting method of the present disclosure, it is preferable that the prosthesis device cut and machined from the dental zirconia for cutting and machining is a crown or a bridge.

Advantageous Effects of Invention

By applying the opaque imparting liquid of the present disclosure to a prosthesis device cut and machined from a dental zirconia for cutting and machining, opaque property is partially imparted to the prosthesis device partially without coloring.

Furthermore, by applying to a pre-sintered body of a pre-colored zirconia, opaque property is imparted to only the applied portion and a masking effect for a discolored tooth is exhibited by adjusting application amount.

DETAILED DESCRIPTION OF THE PREFERRED EMBODIMENTS

Hereinafter, constituent elements in the present disclosure are described in detail.

As the component (a) the water-soluble aluminum compound and/or the water-soluble lanthanum compound contained in the opaque imparting liquid of the present disclosure, any aluminum compound may be used regardless of the degree of the solubility as long as it dissolves in water. Among them, specific examples include lactate, aluminum ethylenediamine tetraacetate, aluminum oxide tartrate hydrate, sodium aluminum citrate, potassium aluminum citrate, aluminum chloride oxide, aluminum citrate, oxy aluminum acetate, oxy aluminum perchlorate, oxy aluminum salicylate, aluminium trichloride, aluminium tribromide, aluminium hydroxide, oxy dialuminum carbonate, oxy aluminium nitrate, aluminium sulfate and aluminium nitrate, and ethylenediamine tetraacetate is particularly preferable. These aluminum compounds may be used alone or in combination of two or more thereof.

In addition, any lanthanum compound may be used regardless of the degree of the solubility as long as it dissolves in water. Preferable lanthanum compounds include lanthanum chloride, lanthanum nitrate, lanthanum sulfate and lanthanum acetate and lantern chloride and lanthanum acetate are particularly preferable.

It is essential that a content of the water-soluble aluminum compound and/or the water-soluble lanthanum compound contained in the opaque imparting liquid of the present disclosure is within a range of 10 wt. % to 39 wt. % and the content is preferably within a range of 20 wt. % to 30 wt. %. When the content of the water-soluble aluminum compound and/or the water-soluble lanthanum compound contained in the opaque imparting liquid is less than 10 wt. %, opaque property is not imparted even if the opaque imparting liquid is applied to a prosthesis device. On the other hand, when the content is more than 39 wt. %, because solubility to water decreases remarkably, it is impossible to prepare an uniform opaque imparting liquid.

The water (b) contained in the opaque imparting liquid of the present disclosure is necessary for dissolution or dispersion of the water-soluble aluminum compound and/or the water-soluble lanthanum compound, and is advantageous for dissolution particularly.

The water contained in the opaque imparting liquid of the present disclosure is not particular limited, but it is possible to use ion exchanged water, Japanese pharmacopeia purified water and Japanese pharmacopeia distilled water and the like. A content of the water contained in the opaque imparting liquid of the present disclosure is not particularly limited, however, is preferably within a range of 60 to 89 wt. % and is more preferably within a range of 65 to 79 wt. %. When the content is little, the solubility of the water-soluble aluminum compound and/or the water-soluble lanthanum compound (a) decreases and when the content is large, the effect by imparting opaque property decreases.

As the organic solvent (c) contained in the opaque imparting liquid of the present disclosure, an organic solvent compatible with the water (b) is appropriately selected and used. It is preferable that the organic solvent acts as a thickener to adjust a viscosity and does not generate a residue as an organic matter in sintering the zirconia. Specific examples of the organic solvent include methanol, ethanol, isopropanol, ethylene glycol, polyethylene glycol, acetone, 1,4-dioxane, polypropylene glycol. Among them, polyethylene glycol and polypropylene glycol are preferable. In addition, a content of the organic solvent contained in the opaque imparting liquid of the present disclosure is not particularly limited as long as within a range of 1 to 20 wt. %, and is preferably within a range of 1 to 5 wt. %. When the content of the organic solvent is less than 0.1 wt. %, application property decreases. When the content is more than 20 wt. %, liquid permeability decreases.

In addition, the opaque imparting liquid of the present disclosure may contain an organic marker based on organic dye. When this opaque imparting liquid is applied to a prosthesis device prepared by cutting and machining a dental zirconia for cutting and machining, it is possible to visualize the applied area and to visualize the applied amount of the opaque imparting liquid and the degree of permeation thereof. It is required for the organic dye not to contain an inorganic matter. Specific examples of the organic dye include *gardenia* yellow pigment, annatto pigment and red cabbage pigment. Among them, red cabbage pigment and *gardenia* yellow pigment are preferable.

When the opaque imparting liquid of the present disclosure is applied to a prosthesis device (semi-sintered body) prepared by cutting and machining a dental zirconia for cutting and machining which is porous and pre-sintered and the applied prosthesis device is perfect sintered, a chroma of a color tone and transparency are improved by the opaque imparting liquid of the present disclosure. Therefore, the opaque imparting liquid of the present disclosure may permeate a prosthesis device which is a pre-sintered body and impart opaque property to the prosthesis device by perfect sintering. In order to exhibit such an effect surely, it is preferable that relative density, specific surface area and composition of a dental zirconia for cutting and machining which is cut and machined for preparing a prosthesis device are adjusted.

Accordingly, it is preferable that the relative density of the a dental zirconia for cutting and machining which is cut and machined for preparing a prosthesis device is within a range of 45 to 60% (when the density of the final sintered body is 100%, the relative density means an apparent density of a semi-sintered body). When the relative density is less than 45%, the machinability with the CAD/CAM machining machine may decrease. On the other hand, when the relative density is more than 60%, there may be a problem that the applied opaque imparting liquid is hard to permeate. In addition, it is preferable that the specific surface area of a dental zirconia blank for cutting and machining is within a range of 10 to 200 $cm^2/g$ from a point of view that a pre-sintered body is porous. When the specific surface area is less than 10 $cm^2/g$, there is a case where the permeation of the opaque imparting liquid is not sufficient, and when the specific surface area is more than 200 $cm^2/g$, there is a case where cutting property with the CAD/CAM machining machine decreases.

In addition, it is preferable embodiment that a dental zirconia for cutting and machining which is cut and machined for preparing a prosthesis device which is applied with the opaque imparting liquid of the present disclosure contains yttrium and/or erbium as a stabilizing material. When the dental zirconia for cutting and machining which is cut and machined for preparing a prosthesis device which is applied with the opaque imparting liquid contains the stabilizing material, aesthetic property is increase. It is preferable that the molar concentration of the stabilizing material contained in the dental zirconia for cutting and machining is 4 mol % or more. It is preferable that the present disclosure is used for a zirconia having high transparency.

It is preferable that a dental zirconia for cutting and machining which is cut and machined for preparing a prosthesis device which is applied with the opaque imparting liquid of the present disclosure is prepared by using colored zirconia powder. Specific examples include zirconia powder containing the above erbium stabilizing material (red) and yellow zirconia powder contained iron. In addition, there is no problem at all even if other colored zirconia powder which contains element such as cobalt (gray), manganese (red), chromic (yellow) for adjusting a color in addition to these colored zirconia powder is used together.

The kind of a prosthesis device applied with the opaque imparting liquid of the present disclosure is not limited particularly, and there is no problem at all even if the prosthesis device is any of an inlay, a laminate, a crown a bridge and the like. Therefore, a shape of a dental zirconia for cutting and machining which is cut and machined for preparing a prosthesis device is not limited particularly, and any dental zirconia for cutting and machining can be used even if the dental zirconia for cutting and machining has any shape such as a block shape corresponding to an inlay, a laminate, a crown and the like and a disk shape corresponding to a bridge. In addition, it is more preferable embodiment that a dental zirconia for cutting and machining which has a multilayered structure and has a block shape or a disk shape for preparing more aesthetic prosthesis device by applying the opaque imparting liquid of the present disclosure.

In addition, the opaque imparting liquid of the present disclosure may be prepared by mixing all components. A liquid form which is in a state with the fluidity is preferable. The state of the opaque imparting liquid is not limited particularly and specific example of the states includes a state where all components are uniformly compatible with, a state where the opaque imparting liquid is divided into a plurality of layers and a state where a specific component is separated and precipitated. There is no problem particularly as long as the whole is in a uniform state by an operation such as shaking before use. Among them, a liquid form which has fluidity and low viscosity and in which all components are compatible with is preferable from a point of view that the opaque imparting liquid of the present disclosure permeates after applying the opaque imparting liquid of the present disclosure to a prosthesis device. For example, the opaque imparting liquid of the present disclosure can only adjust transparency to impart opaque property only to a portion where the opaque imparting liquid is applied by applying to the inner surface of the prosthesis device cut and machined from a dental zirconia for cutting and machining.

EXAMPLES

The present disclosure is described in more detail and specifically with reference to Examples. However, the present disclosure is not limited to Examples.

The opaque imparting liquids containing components shown in following Examples and Comparative Examples were prepared as the zirconia opaque imparting liquid. The preparation was performed by mixing each reagents with a solvent for one hour. Semi-sintered zirconia piece having a dimension of 10 mm×10 mm×1 mm was cut out from "SHOFU DISK ZR Lucent FA super light color" manufactured by SHOFU INC. as a zirconia disk imparted with opaque property. Thereafter, the opaque imparting liquids described in Examples and Comparative Examples were applied by a writing brush to the piece. The piece was sintered by the method described in the manual. In addition, opaque property was evaluated by calculating based on the visible light transmissivity in case of not applying the opaque material when the visible light transmissivity in case of not applying the opaque materials was 100. For the application property of the opaque imparting liquid was evaluated by ○, Δ, x. The rating criteria were as follow:

○: Applicable by writing brush.
Δ: Viscosity was slightly low and it was hard to apply.
x: Not cling to writing brush and it was hard to apply.

In the measurement of the bending test body, test specimens having dimensions of a width of 4.8 mm, thickness of 1.6 mm and length 20 mm were prepared by cutting and machining "SHOFU DISK ZR Lucent FA super light color" manufactured by SHOFU INC. as the dental zirconia for cutting and machining. The opaque imparting liquids described in Examples and Comparative Examples were applied on only one side of the test specimen. Thereafter, the test specimen was sufficiently dried at 80° C. for one hour. Further, test specimen was sintered by retaining at 1450° C. of final retaining temperature for two hours according to the method described in the manual. Three point bending test was performed for the test specimen so that tensile stress was applied the surface applied with the opaque imparting liquid. In addition, the test method was based on ISO 6872-2015.

In addition, in comparative example 1, measurement was performed without the opaque imparting liquid.

TABLE 1

| | | Example 1 | Example 2 | Example 3 | Example 4 | Example 5 | Example 6 | Example 7 |
|---|---|---|---|---|---|---|---|---|
| Component (a) | Aluminum nitrate | 20.0 | | | 30.0 | | | |
| | Aluminum acetate | | 30.0 | | | 20.0 | | |
| | lanthanum acetate | | | 20.0 | | | 30.0 | |
| | aluminum ethylenediamine tetraacetate | | | | | | | 20.0 |
| Component (b) | Water | 77.9 | 67.9 | 77.9 | 67.9 | 77.9 | 67.9 | 77.9 |
| Component (c) | Glycerin | 2.0 | | 2.0 | 2.0 | | 2.0 | 2.0 |
| | Polyethylene glycol | | 2.0 | | | 2.0 | | |
| Coloring material | Red cabbage pigment | 0.1 | 0.1 | 0.1 | 0.1 | 0.1 | 0.1 | 0.1 |

| | | Example 8 | Example 9 | Example 10 | Example 11 | Example 12 | Example 13 | Example 14 |
|---|---|---|---|---|---|---|---|---|
| Component (a) | Aluminum nitrate | 30.0 | 20.0 | 20.0 | | 10.0 | 37.9 | 20.0 |
| | Aluminum acetate | | | | 30.0 | | | |
| | lanthanum acetate | | | | | | | |
| | aluminum ethylenediamine tetraacetate | | | | | | | |
| Component (b) | Water | 67.9 | 77.9 | 75.0 | 68.9 | 88.9 | 60.0 | 60.0 |
| Component (c) | Glycerin | | | 5.0 | | | | |
| | Polyethylene glycol | 2.0 | 2.0 | | 1.0 | 1.0 | 2.0 | 19.9 |
| Coloring material | Red cabbage pigment | 0.1 | 0.1 | | 0.1 | 0.1 | 0.1 | 0.1 |

| | | Comparative Example 1 | Comparative Example 2 | Comparative Example 3 | Comparative Example 4 |
|---|---|---|---|---|---|
| Component (a) | Aluminum nitrate | | 5.0 | 5.0 | 50.0 | 10.0 |
| | Aluminum acetate | | | | | |
| | lanthanum acetate | | | | | |
| | aluminum ethylenediamine tetraacetate | | | | | |
| Component (b) | Water | | 92.9 | 92.9 | 47.9 | 89.9 |
| Component (c) | Glycerin | | 2.0 | | 2.0 | |
| | Polyethylene glycol | | | 2.0 | | |
| Coloring material | Red cabbage pigment | | 0.1 | 0.1 | 0.1 | 0.1 |

| | Example 1 | Example 2 | Example 3 | Example 4 | Example 5 | Example 6 | Example 7 |
|---|---|---|---|---|---|---|---|
| Opaque effect | 55 | 33 | 56 | 36 | 60 | 40 | 60 |
| Application property | A | A | A | A | A | A | A |
| Bending strength [MPa] | 995 | 960 | 998 | 940 | 970 | 966 | 890 |

TABLE 1-continued

|  | Example 8 | Example 9 | Example 10 | Example 11 | Example 12 | Example 13 | Example 14 |
|---|---|---|---|---|---|---|---|
| Opaque effect | 65 | 45 | 46 | 61 | 45 | 66 | 51 |
| Application property | A | A | A | A | A | A | A |
| Bending strength [MPa] | 910 | 995 | 996 | 905 | 906 | 910 | 920 |

|  | Comparative Example 1 | Comparative Example 2 | Comparative Example 3 | Comparative Example 4 |
|---|---|---|---|---|
| Opaque effect | 100 | 95 | 30 | 95 |
| Application property | A | A | A | C |
| Bending strength [MPa] | 1016 | 1019 | 676 | 995 |

Consideration of Examples

An opaque effect was sufficiently exhibited in Examples 1-14 in comparison with Comparative example 1. When the opaque effect was 70 or less, the application effect was exhibited and it was useful clinically. On the other hand, in Comparative example 2, the amount of the component (a) was little and the opaque effect was few. In addition, in Comparative example 3, although the opaque effect was recognized, the bending strength remarkably decreased. In comparative example 4, application property was wrong and it was hard to use clinically.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present disclosure relates to an opaque imparting liquid to exhibit opaque property on a zirconia ceramic prosthesis device after sintering by applying to a prosthesis device cut and machined from a dental zirconia for cutting and machining by using a CAD/CAM system in a dental field and can be applied in industries.

What is claimed is:

1. An opaque imparting liquid used for a prosthesis device cut and machined from a dental zirconia for cutting and machining, consisting of:
   (a) 10 to 39 wt. % of a water-soluble aluminum compound and/or a water-soluble lanthanum compound,
   (b) 60 to 89 wt. % of water, and
   (c) 1 to 20 wt. % of an organic solvent, wherein the opaque imparting liquid further consists of an organic marker.

2. The opaque imparting liquid according to claim 1, wherein
   the organic solvent (c) contains a member selected from the group consisting of alcohols, polyol and glycol ethers.

3. The opaque imparting liquid according to claim 1, wherein
   the water-soluble aluminum compound and/or the water-soluble lanthanum compound (a) contains aluminum acetate and/or lanthanum acetate.

4. The opaque imparting liquid according to claim 1, wherein
   the dental zirconia for cutting and machining is colored by a zirconia powder where iron, erbium and/or cobalt is solid-solved.

5. An opaque imparting method comprising;
   applying the opaque imparting liquid according to claim 1 only to an inner surface of a prosthesis device cut and machined from a dental zirconia for cutting and machining.

6. The opaque imparting method according to claim 5, wherein
   the prosthesis device cut and machined from the dental zirconia for cutting and machining is a crown or a bridge.

7. The opaque imparting liquid according to claim 2, wherein
   the water-soluble aluminum compound and/or the water-soluble lanthanum compound (a) contains aluminum acetate and lanthanum acetate.

8. The opaque imparting liquid according to claim 2, wherein
   the dental zirconia for cutting and machining is colored by a zirconia powder where iron, erbium and/or cobalt is solid-solved.

9. The opaque imparting liquid according to claim 3, wherein
   the dental zirconia for cutting and machining is colored by a zirconia powder where iron, erbium and/or cobalt is solid-solved.

10. An opaque imparting method comprising;
    applying the opaque imparting liquid according to claim 9 only to an inner surface of a prosthesis device cut and machined from a dental zirconia for cutting and machining.

11. The opaque imparting method according to claim 10, wherein
    the prosthesis device cut and machined from the dental zirconia for cutting and machining is a crown or a bridge.

12. An opaque imparting method comprising;
    applying the opaque imparting liquid according to claim 2 only to an inner surface of a prosthesis device cut and machined from a dental zirconia for cutting and machining.

13. The opaque imparting method according to claim 12, wherein
the prosthesis device cut and machined from the dental zirconia for cutting and machining is a crown or a bridge.

14. An opaque imparting method comprising;
applying the opaque imparting liquid according to claim 3 only to an inner surface of a prosthesis device cut and machined from a dental zirconia for cutting and machining.

15. The opaque imparting method according to claim 14, wherein
the prosthesis device cut and machined from the dental zirconia for cutting and machining is a crown or a bridge.

16. An opaque imparting method comprising;
the opaque imparting liquid according to claim 4 is applied only to an inner surface of a prosthesis device cut and machined from a dental zirconia for cutting and machining.

17. The opaque imparting method according to claim 16, wherein
the prosthesis device cut and machined from the dental zirconia for cutting and machining is a crown or a bridge.

* * * * *